United States Patent [19]

Choy

[11] 4,230,689
[45] Oct. 28, 1980

[54] HAIR GROOMING COMPOSITION OF MATTER

[76] Inventor: Sue Choy, 4109 Whispering La., Annandale, Va. 22003

[21] Appl. No.: 34,980

[22] Filed: May 1, 1979

[51] Int. Cl.³ .............................................. A61K 7/06
[52] U.S. Cl. ...................................... 424/74; 424/195
[58] Field of Search ................................. 424/74, 195

[56] References Cited

U.S. PATENT DOCUMENTS 285,045   9/1833   Leip ....................................... 424/74

FOREIGN PATENT DOCUMENTS 42-7279   3/1967   Japan ........................................ 424/74
46074     2/1929   Norway .................................... 424/74

*Primary Examiner*—Dale R. Ore

[57] ABSTRACT

A novel composition of matter is disclosed which comprises the vaporous gas of a heated hydrate admixture of about 1 part of a starch, 0.1 to 2 parts of mung bean and an aqueous solution of ginseng root.

3 Claims, No Drawings

HAIR GROOMING COMPOSITION OF MATTER

This application relates to a novel composition of matter which is useful in the grooming and maintenance of human hair. A specific embodiment of this invention resides in a hair-grooming composition of matter comprising the vaporous gas of a heated admixture of about 1 part white rice, about 0.25 parts mung bean and an aqueous solution of ginseng root.

Another embodiment of this invention resides in a composition of matter which is the vaporous gas or the condensation of the same of a heated admixture of about one part of white rice, about 2.5 parts of mung bean and an aqueous solution of ginseng root.

An object of this invention is to provide a composition of matter which acts as a beneficial media for grooming of the human hair, both male and female.

Candor compels a recognition of the prior art in regards to this composition of matter. Some compositions of matter containing plant material of undetermined composition as the active ingredient are classified in Class 424, subclass 195+. Hair grooming compositions of matter of natural origin are also concerned with Class of 424, subclass 74 which relates to hair treatment compositions containing esoteric formulae. Of the prior art known to this subclass the following is believed a recitation of particular techniques for obtaining various hair grooming or shampoo compositions of matter.

U.S. Pat. No. 604,111 relates to a disclosure comprising a decoction of mountain-sage, glycerin, tincture of Lobelia, prickly pear juice, tincture of capsicum, sweet-oil, and alcohol. U.S. Pat. No. 1,508,785 relates to a hair tonic comprising an aqueous extract of tea, cinnamon bark and oats with alcohol as a preservative. U.S. Pat. No. 285,045 disclosed a hair tonic comprising an infusion of potatoes, onions and sage in particular proportions.

Of somewhat more recent vintage is U.S. Pat. No. 3,809,747, which claims a solution for scalp treatment made in accordance with process steps set forth as dispersing from one to five medium size chili peppers and one-half to one medium size lemon in a quart of water and boiling same for fifteen to thirty minutes to provide natural oil juices and pulps from which pulp is removed to obtain a clear solution. In U.S. Pat No. 3,932,611 a composition for hair and scalp care is disclosed which comprises white petroleum jelly, beeswax, coconut oil, olive oil, castor oil, oil of sassafras, and oil of cinnamon. In U.S. Pat. No. 3,980,768 a composition for hair care was disclosed which included petrolatum, sulfur, quinine powder, egg yolks, essence of spice, and alcohol. Also, U.S. Pat. No. 3,984,538 disclosed a hair shampoo containing an extract of chamomile in combination with urea. Thus, the Patent Office has recognized novel mixtures of natural components for hair care. Also, the patent literature has recognized that various process steps involving natural or plant components can result in compositions of matter that are both novel and unobvious even though the exact chemical constituency of the final product is not exactly known. Likewise, these admixtures have long been accepted as useful in the treatment of hair and scalp disease. This application contains a description of a composition of matter prepared by specific process steps in order to obtain a clear liquid which is useful in hair grooming and scalp care.

The composition of matter is a condensation product which is a clear liquid. This condensate is recovered by the following steps: An admixture is made comprising starch and mungbean in a proportion of one part starch to 0.1 part to 2 parts mungbean. This admixture is allowed to completely hydrate to the saturation point and at that time is heated to a temperature of about 75° F. to about 212° F. in the presence of an aqueous solution of a root of an arailiaceous plant. This particular heating step may be conducted over various periods of time with the only limitation being that where the temperature is maintained near the higher level of 212° F., the period of time necessary to derive the composition of matter is of less duration than the time required when utilizing a temperature closer to the lower end temperature or 75° F. After this mixture is heated, it is encapsulated within a closed environment to provide a means to acquire the condensate of the vapors of the heated admixture above specified. The recovery of these vapors may occur over a period of time such as overnight, and the same has been found to be a novel and unobvious hair grooming composition of matter.

The hydration step should be made to substantially saturate the starch and mungbean with water. The starch component can comprise any variable known starch, however, the preferred starch is most preferably white rice. Other rice such as brown rice, sweet brown rice, long grain brown rice, and wild rice may also be used as a substitute for the white rice. Other members of the starch family such as potatoes may also be used to obtain the desired admixture. Mungbean is recognized as a stable commodity available in most food establishments and is botanically known as phaseolus aureus. The proportion of mungbean to starch is anywhere from 1 part of starch to 0.1 to 2 parts mungbean. After this substantial hydration, the admixture is heated to a specified temperature of about 75° F. to about 212° F. in the presence of an aqueous solution of a root of an arailiaceous plant. This arailiaceous plant is preferably ginseng and most preferably ginseng derived from a Korean ginseng plant, although some species of the U.S. ginseng plant are also adequate, such as those derived in West Virginia. Other material which may also be used are hemp root, maidenhair root, rosemary, cherrybark, comfrey leaf, licorice root and spikenard. After the admixture has been heated the same is encapsulated within a closed system, such as placing a lid upon the container holding the admixture. It is also contemplated that the heated admixture can be transferred to a separate container and covered to obtain the condensate.

One preferred method of preparing this material is found in the fact that the container possesses a metal bottom such as brass or sterling silver. It is believed that this material will aid in the transfer of heat and the inner cooperative action of the three components, namely starch, mungbean, and the aqueous solution of a root plant.

ILLUSTRATIVE EMBODIMENT

A specific method of preparing this composition is as follows: one cup of white rice and 1/5 cup of mungbean are washed and soaked and let stand in water overnight until the grains are completely softened and saturated. They are subsequently washed and boiled in a pot with one cup of pure water and one cup of white ginseng tea water cooked to the boiling point. The admixture after boiling, is allowed to simmer for five minutes and thereafter placed in a brass container having a tight cover. After a period of time of two to five hours the cover is removed and the liquid deposited thereon is carefully collected as the hair treating composition of matter. The technique of using this clear liquid is relatively simple. A small portion of the amount of the material should be poured into the palm of the hand and the same applied to the hair and scalp with vigorous rubbing. While it is beneficial to the scalp and hair grooming to apply this material intermittently, it is believed of benefit to the recipient that the same be used everyday or every other day for a period of time of a few weeks to a few months. After this period of time the recipient will notice a better color tone to his or her hair and a cleaning of the scalp without any residual grease disposed therein.

The aforementioned specification is not to be unduly limited upon the claims hereinafter set forth and any equivalent material to that recited in the claims is believed within the scope of this composition of matter.

What is claimed is:

1. A composition of matter for use in the grooming of human hair, which composition is prepared by the process which comprises the steps of:

(a) hydrating with water to hydration an admixture of 1 part white rice with 0.1 to 2 parts mung bean;
    (b) heating said admixture to a temperature of about 75° F. to about 212° F. in the presence of 1 cup of Ginseng tea;
    (c) enclosing said heated admixture in a closed environment to provide a means to acquire the condensate of the vapors of said heated and enclosed admixture; and
    (d) recovering said condensate of said heated and enclosed admixture as said hair grooming composition of matter.

2. The composition of matter of claim 1 wherein said admixture of step (b) is brought to a boil and allowed to simmer for a period of time ranging from ½ to 30 minutes.

3. The composition of matter of claim 1 wherein said heated admixture is permitted to remain in said closed environment for a period of time ranging from 178 to 25 hours.

* * * * *